United States Patent [19]

Roussigne et al.

[11] Patent Number: 5,630,801
[45] Date of Patent: May 20, 1997

[54] DEVICE FOR IMPLANTING A MEDICAL PROSTHESIS IN A DUCT OF A HUMAN OR ANIMAL BODY

[75] Inventors: Maurice Roussigne; Guy Nadal, both of Poitiers; Gérard Chevillon, Montrouge, all of France

[73] Assignee: B. Braun Celsa, Chasseneuil, France

[21] Appl. No.: 314,649

[22] Filed: Sep. 29, 1994

[30] Foreign Application Priority Data

Oct. 5, 1993 [FR] France .................. 93 11851

[51] Int. Cl.⁶ .................................................. A61M 37/00
[52] U.S. Cl. ........................... 604/95; 623/1; 606/108; 606/195
[58] Field of Search ........................ 606/108, 195; 604/4–6, 281, 95; 623/1, 2, 11; 128/772, 200.26, 900

[56] References Cited

U.S. PATENT DOCUMENTS

| 4,033,331 | 7/1977 | Guss et al. . |
| 4,643,184 | 2/1987 | Mobin-Uddin . |
| 4,925,445 | 5/1990 | Sakamoto et al. ............... 604/95 |
| 4,983,169 | 1/1991 | Furukawa . |
| 4,990,156 | 2/1991 | Lefebvre . |
| 5,120,308 | 6/1992 | Hess ............................ 128/772 |
| 5,174,379 | 12/1992 | Sabbaghian et al. . |
| 5,211,183 | 5/1993 | Wilson . |
| 5,235,970 | 8/1993 | Augustine . |
| 5,456,713 | 10/1995 | Chuter ......................... 606/195 |

FOREIGN PATENT DOCUMENTS

| 0531946 | 3/1993 | European Pat. Off. . |
| 2657261 | 7/1991 | France . |
| WO90/13329 | 11/1990 | WIPO . |

Primary Examiner—Robert A. Clarke
Attorney, Agent, or Firm—Pollock, Vande Sande & Priddy

[57] ABSTRACT

The invention relates to a device for implanting a medical prosthesis in a duct of a human or animal body.

Thin device comprises a tubular sheath, suitable for containing a prosthesis to be implanted, and a rod for controlling the prosthesis, which rod may slide in the interior of the sheath. The sheath and/or the rod is(are) provided on at least one part of its (their) length with flexible centring means suitable for acting on the profile of the axial line of the sheath, while restricting its distal end to align itself substantially with the axis of the duct when the sheath is disposed therein.

The application of the invention is most particularly in the field of blood filters which can be implanted in a blood vessel.

8 Claims, 7 Drawing Sheets

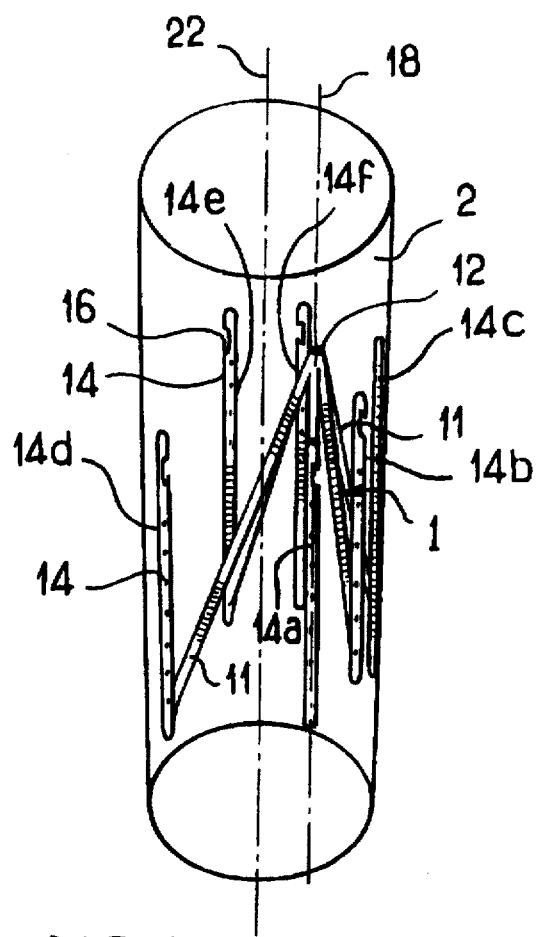
FIG_1
PRIOR ART
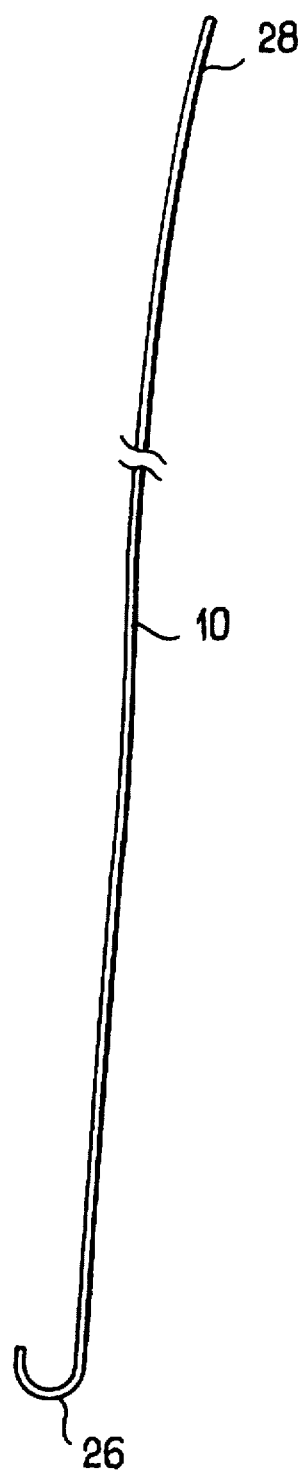
FIG_2
PRIOR ART

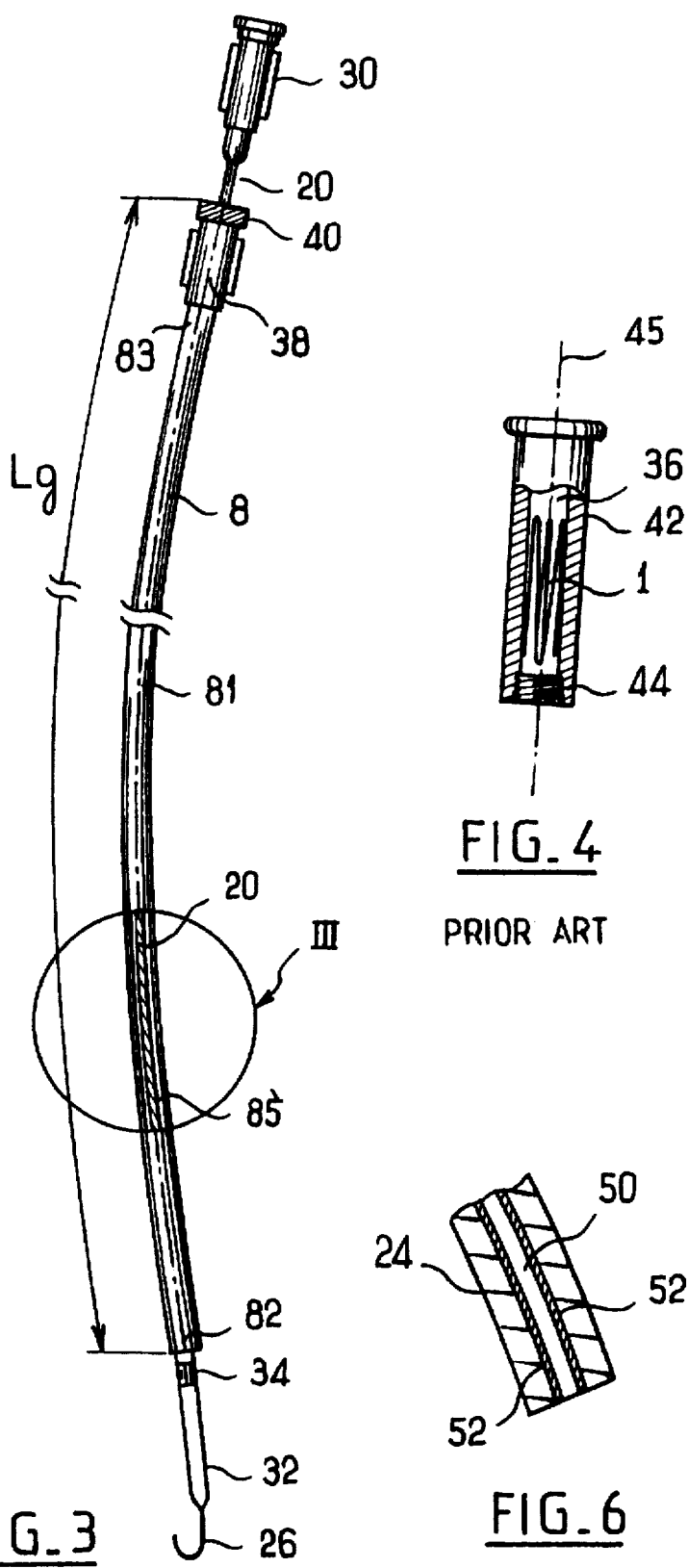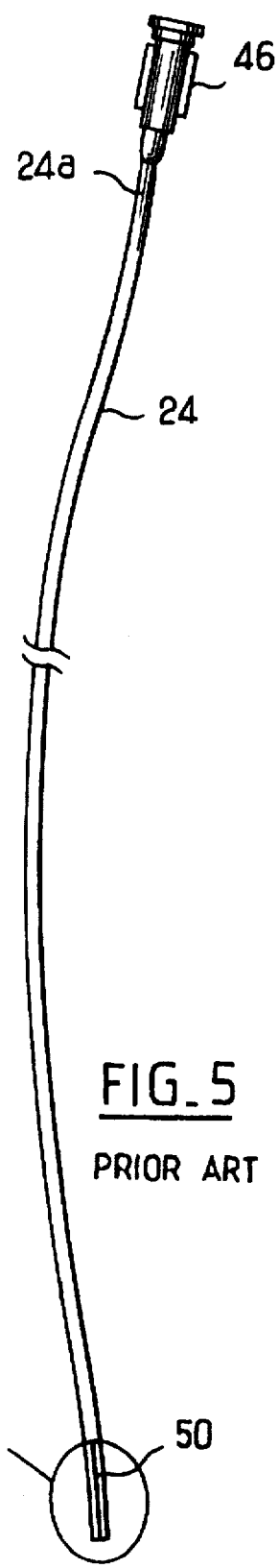
FIG. 3 PRIOR ART
FIG. 4 PRIOR ART
FIG. 6 PRIOR ART
FIG. 5 PRIOR ART

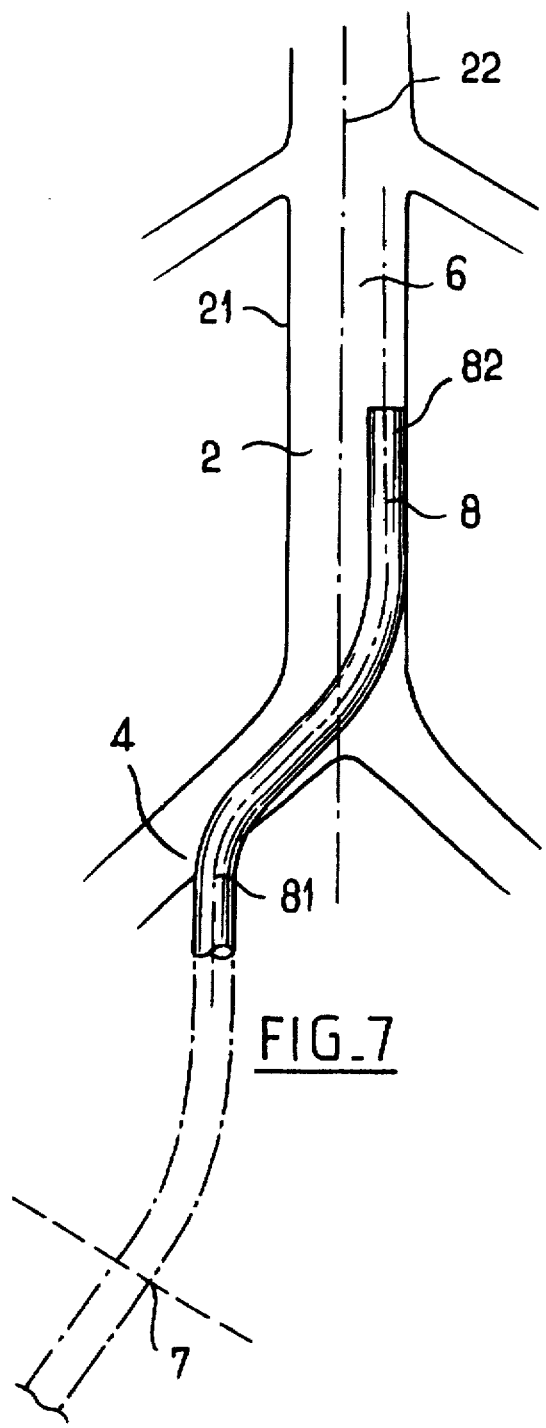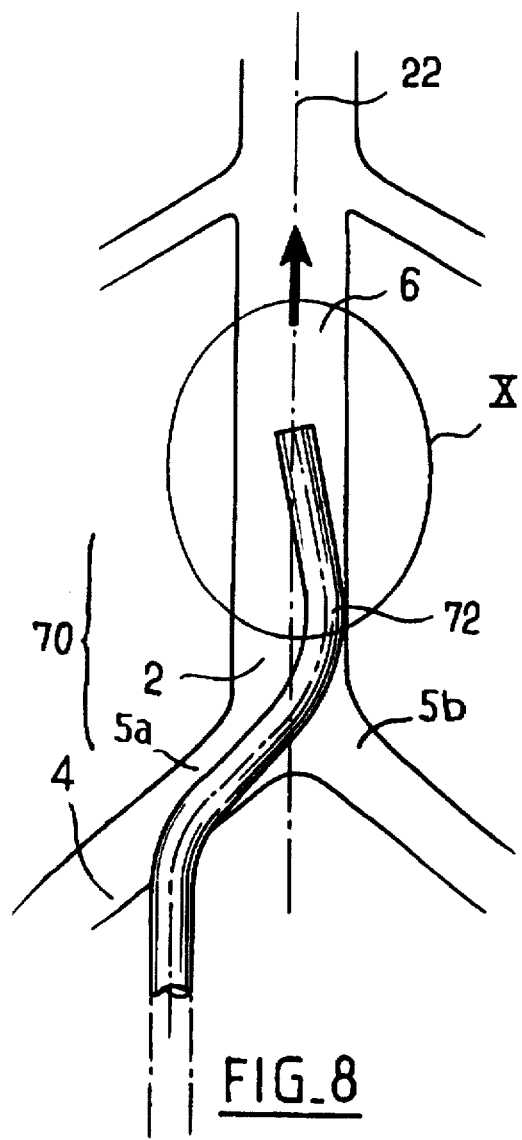

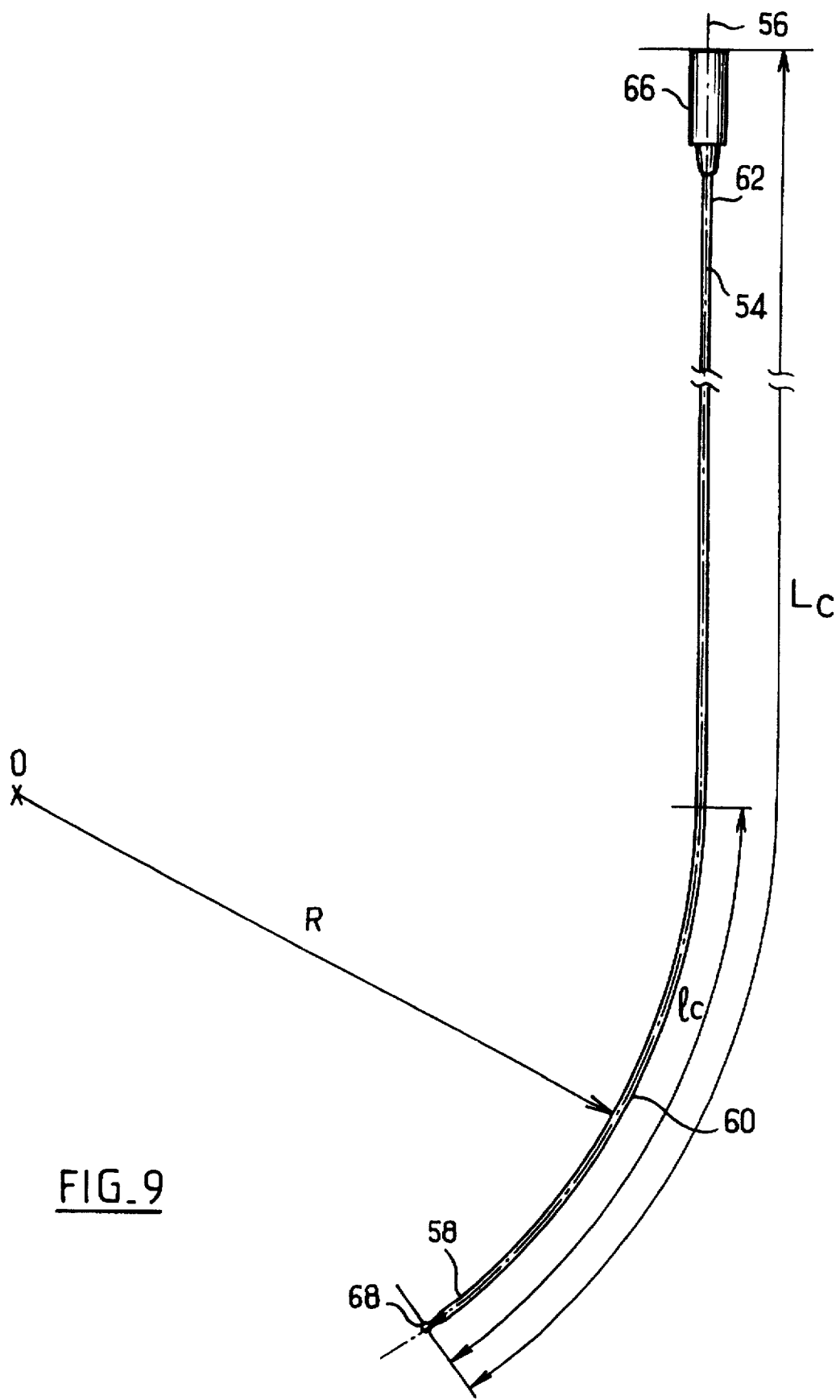
FIG_9

FIG_11
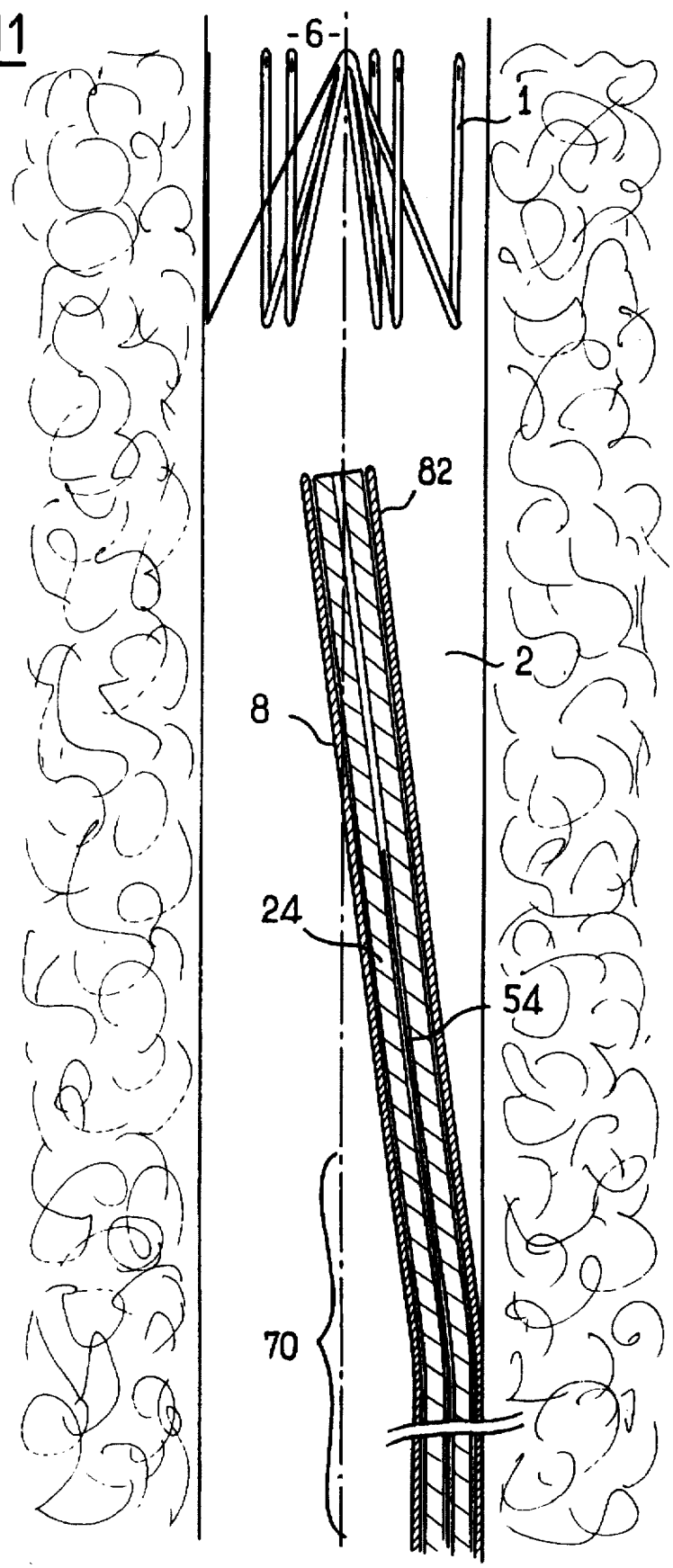

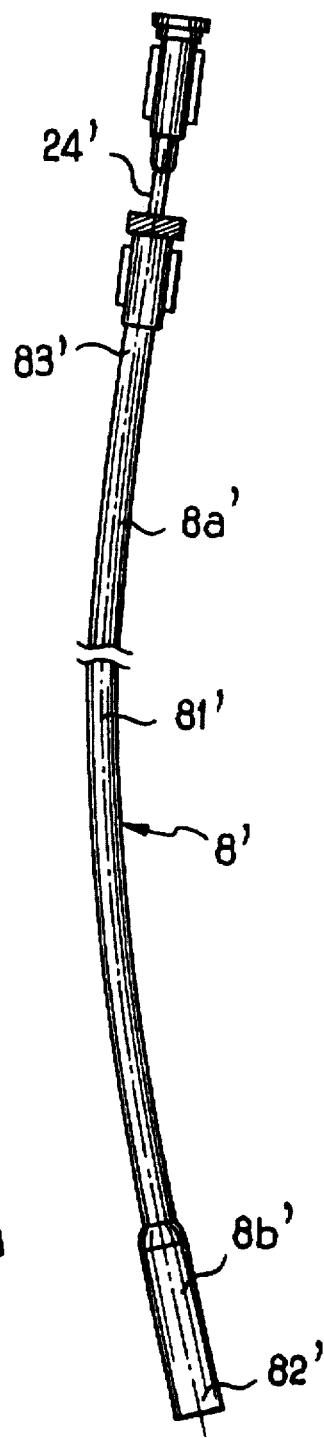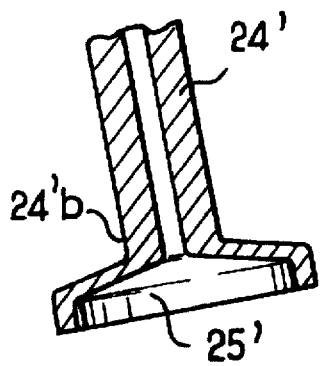

DEVICE FOR IMPLANTING A MEDICAL PROSTHESIS IN A DUCT OF A HUMAN OR ANIMAL BODY

FIELD OF THE INVENTION

The subject of the invention is in particular, a device for improving the implantation of a prosthesis in an internal duct of a living animal or human body.

BACKGROUND OF THE INVENTION

The invention is used in the medical field, when it is necessary to implant a prosthesis in a given area of a duct of a patient's body. More particularly, the invention may be used for the insertion of a blood filter into a vessel in order to retain blood clots which maybe present.

Devices of this type are known and described in patent application FR-A-2 657 261, for example. In general, the device comprises a tubular sheath inserted into the duct over the desired length to extend as far as the area where the prosthesis is implanted. This sheath is usually produced of a supple material so that it can adapt easily to sinuous paths; it is thus easy to position using a guide thread and an introducing tube. This device likewise comprises a control rod, suitable for sliding in the sheath and for causing the prosthesis to slide therein, which prosthesis may this be directed towards the area of implantation where it may then be expelled to the outside of the sheath to implant itself in the duct by unfolding itself there.

The checks which are usually performed after the implantation of the prosthesis, to ensure the correct insertion thereof in the duct, have shown that the prosthesis is sometimes incorrectly positioned in the duct and there is thus a risk that it will not perform its function correctly.

These problems have been observed most particularly in the field of blood filters.

Among these filters, there are those which currently have, in the unfolded position, the general form of a small frustoconical basket comprising a plurality of resilient fingers, and which may be folded back on themselves to be introduced easily into the interior of their implanting device. Filters of this type are often positioned in the inferior vena cava, by the percutaneous method Of access or by "stripping", either in the vicinity of the jugular vein (via the superior vena cava) or in the vicinity of one of the femoral veins. It is in particular in the latter case, where an introduction is performed via the femoral route, that it has been established that there is sometimes an asymmetrical opening of the filters in the vessels, even if "auto centering" filters, i.e. those which are intended to unfold themselves naturally with their longitudinal axis substantially merged with that of the vessel, are used. This incorrect opening is detrimental, particularly for filters called "definitive" or "permanent" filters, which are provided with a means of anchoring to the wall of the vessel and the position of which can thus in practice not be corrected after the opening of the filter.

BRIEF DESCRIPTION OF THE INVENTION

Confronted by these problem, the applicants, instead of seeking, as would be logical, to further improve the autocentering capacity of expandable filters or, more generally, the centering properties of prosthesis, have, on the contrary interested themselves in the device used for the implantation thereof. They have been able to establish that, in particular, the external sheath, which is necessary for the implantation, is sometimes flattened against the wall of the duct, at least in the end part thereof. This has in particular been established during implantations of blood filters in the inferior vena cava, by the femoral route, where the left and right iliac veins respectively form a bend with the vena cava, thus defining a vein path which is curved substantially in the form of an "S".

It has been deduced that this offsetting or this oblique end positioning of the implanting device may constitute a significant disadvantage insofar as this may explain why the prosthesis, once it has been ejected to the outside of the sheath, then tends to position itself transversely in relation to the axis of the duct, with inherent risks which may be imagined (damage to the vessel wall, reduced efficiency of the prosthesis, increased risks of travel, etc).

It is against this background that the invention proposes an implanting device, comprising:

a tubular implanting sheath, adapted to be able to contain, at least locally, a prosthesis to be implanted, the sheath, which is extended along an axial line, with an internal passage, having a distal end and being flexible over at least part of its length;

the stem for controlling the prosthesis, the rod being at least partly flexible, and of an exterior diameter which is suitable for sliding in the sheath; this device is characterized in that the sheath and/or the rod is (are) provided or even equipped on at least one part of its (their) length, with flexible centering means suitable for acting on the profile of the axial line of the sheath, by restricting its distal end to orientating itself towards the axis of the duct when the sheath is disposed therein.

For all useful purposes, it should be noted that the expression "distal end" designates the end which is implanted the deepest in the duct, it being understood that the "proximal end" is the opposite which must be located outside the body of the patient.

Advantageously, the centering means which are provided according to the invention are mounted in a sliding manner inside the sheath, to restrict, by reaction and from a distance, the orientation of, in particular, the distal end of the sheath, the latter being, in the context of its application, in fact subjected to restrictions exerted on it at the same time by the centering means and by its environment once it is implanted.

In practice, in place of "centering means" or "restricting means", the use of a relatively fine and flexible cable is advised, which cable is preferably mounted in a sliding manner in the interior of the control rod which is hollow in this case. The cable may be produced of a metallic material or equivalent, naturally curved, or even of a material with a heat-sensitive "shape memory".

In addition to the device for implanting a prosthesis in itself, the invention also relates to a process for centering this device, in which:

a tubular sheath extending along an axial line is introduced into the duct, this sheath having a distal end and being flexible over at least one part of its length, containing, in a sliding manner, an internal rod, which is at least partly flexible, for controlling the position of the prosthesis, and the profile of the axial line of the sheath is acted on in that the sheath is provided or equipped with flexible restraining means acting on it to restrain at least the distal end thereof in order to direct it towards the axis of said duct.

BRIEF DESCRIPTION OF THE FIGURES

The invention and the application thereof will be shown more clearly with the aid of the description which follows and which is made with reference to the attached drawings which are given solely byway of example. In the drawings:

FIG. 1 is a perspective view showing the implantation of the medical prosthesis of a known type;

FIG. 2 is an elevational view of a guide thread, as employed in the prior art.

FIG. 3 is a partial sectional view of an implanting device, as employed in the prior art.

FIG. 4 is a detailed sectional view of a syringe and enclosed filter, in accordance with the prior art.

FIG. 5 is an elevational view of a control rod, as employed in the prior art.

FIG. 6 is a partial cross-sectional view of the control rod, as depicted in FIG. 5.

FIGS. 6 is a schematic enlarged sectional view of the detail designated VI in FIG. 5;

FIG. 7 is a schematic view, partially in section, illustrating the position of the sheath which has permitted the implantation of the prosthesis in FIG. 1 according to the prior art;

FIG. 8 shows the corrected position the sheath in FIG. 7 in place in its duct;

FIG. 9 shows, on a larger scale, an embodiment of the centering cable of the device according to the invention, used conjointly with the other elements shown in FIGS. 2 to 6;

FIG. 11 shows, together with FIG. 10, two successive stages of the positioning of a medical prosthesis by means of the device according to the invention;

FIG. 12 shows the shape assumed, in an ambient temperature, by a cable according to the invention which is produced from a material with a thermal shape memory;

FIG. 13 shows the cable in FIG. 12 at a higher temperature;

FIG. 14 shows the variant of the embodiment of the sheath in FIG. 3 and the control stem in FIG. 5; and FIG. 15 is an enlarged sectional view of the distal end of the stem in FIG. 14.

DETAILED DESCRIPTION OF THE INVENTION

Figure 10:
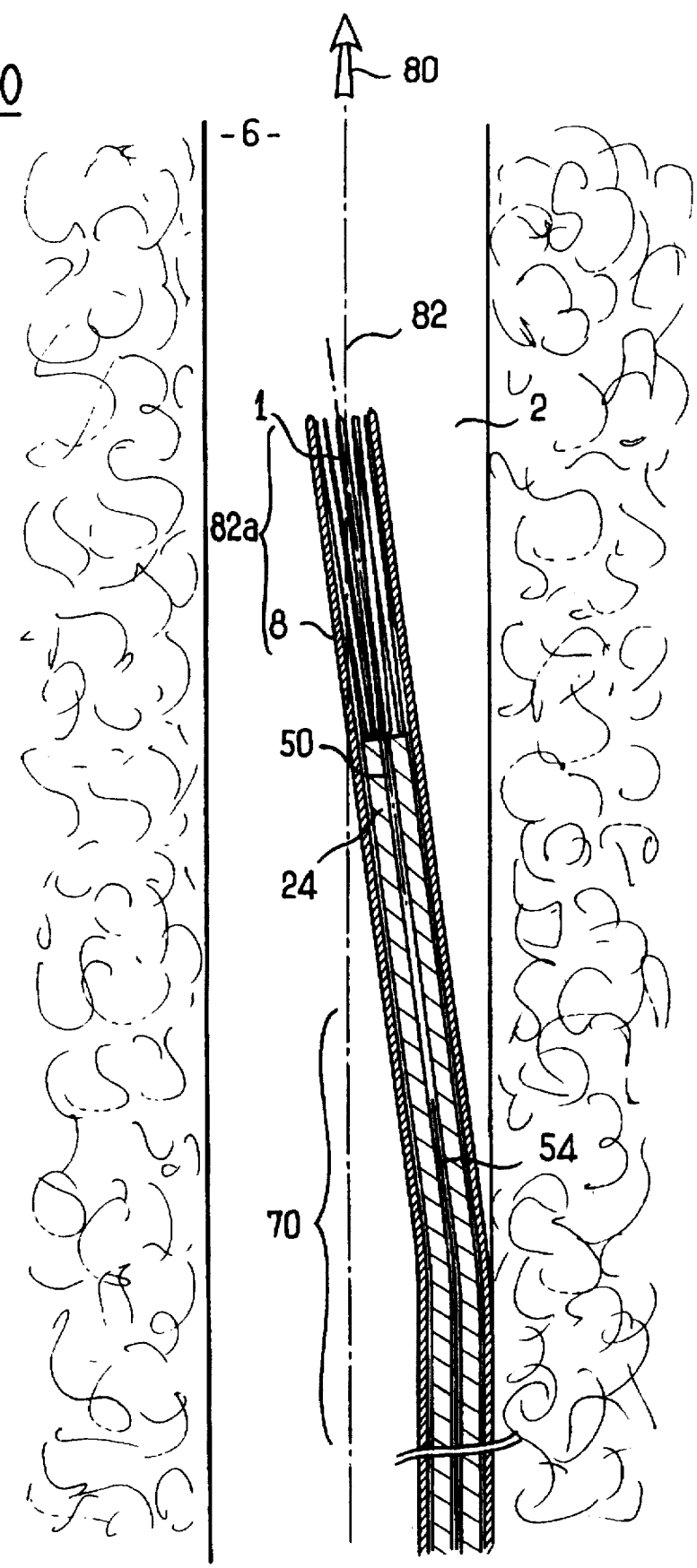
FIG. 10 is a sectional view of the detail designated in X in FIG. 8.

One of the advantages Of using the device according to the invention is being able to implant a "definitive" blood filter in a substantially centered position in a blood vessel (usually a vein). The invention is only described hereinbelow in the context of an application of this type, even though it is obvious that it may be used for the Implantation of other filters, or even other prosthesis (such as "stents" for even if they are not vascular (prostatic prosthesis for example).

Reference is now made to FIGS. 1 to 7 showing the position of this type of filter positioned in the conventional manner, as well as a device of the known type.

In the example shown, FIG. 1 shows a blood filter 1, of the known type described in Patent FR-A-2 573 646 for example, implanted in the inferior vena cava 2 of a patient. This auto centring and definitive filter is formed of six resilient fingers 11, extending from a common head 12, and unfoldable (or auto expandable) in a radial manner following a conical corolla. These fingers are provided with centering appendages 14 to encourage the centring of the filter in the axis of the vessel. Each appendage comprises a hook 16 for securing the filter to the wall of the blood vessel duct 2.

The filter is here shown incorrectly positioned in the duct 2, the longitudinal axis 18 of the filter being offset in relation to the axis 22 of the vessel.

Referring now to FIGS. 2 to 6, there are shown different known constructive elements of a device which can be used for the positioning of the filter 1. This device essentially comprises a guide thread 10 and a guide 20 which allows a long sheath 8 to be inserted into the vein, in such a manner that the distal end 82 thereof arrives at the location of the implantation of the filter, which filter is supplied, through the sheath, by means of a control stem 24. These elements of the device, with the exception of the guide thread which is preferably metallic, are, a priori, made of biocompatable plastics material, for example, of polyolefins. They are, in all events, sufficiently supple or flexible to be able to slide along the access zests without risking damaging the tissues.

The fine guided thread 10, which may have a diameter of the order of a millimeter, has a distal end 26 which is curved in a "J" shape in order not to cause damage during the displacement thereof.

The tubular guide 20 has an interior axial passage the diameter of which is slightly greater than that of the guide thread 10, in order to allow it to be fitted onto the thread such that it can slide. This guide furthermore comprises, at its proximal end, a widened tubular head 30, and, at its distal end 32, which has an ogival shape, a radio-opaque marker 34 (such as a metal ring).

The sheath 8 is in the form of a hollow cylindrical tube, with an axis 91 and an inner passage 85 (shown in the circled part III in FIG. 3, showing an area of the sheath in section). The inner diameter of the sheath is adapted such that the guide 20, or the control stem 24, may slide therein with a slight radial and that the filter, in the retracted position, may slide without significant radial play. This sheath, which is preferably of constant axial rigidity, has a length of Lg along the axial line 81 thereof, which is adapted for the radio-opaque marker 34 to project at its end 82 when the guide is totally inserted into the interior passage thereof. At its proximal end 83, it comprises enlarged hollow piece 38 which has, at its free end, a thread 40.

Furthermore the device comprises a syringe body 42 of plastics material, having the form of a hollow tube open at its opposite ends and provided, at its distal end 44, with an inner thread which is complementary to that of the hollow piece 38. This syringe body 42 may be accommodated, in its entirety, in its internal passage 36, the filter 1 which is in the retracted position, the axis 18 of which is thus substantially merged with the axis 45 of the body.

As regards the control rod 24, the length of which is, in practice, slightly greater than that of the sheath, it is terminated at its proximal end 24a by a widened hollow nozzle 46 which may be hollow piece in that 38 of the sheath. Advantageously, the control rod 24 is hollow for the sliding, through its Anterior passage 50, of a centering cable 54 described hereinbelow or, optionally, for the injection of a fluid medication into the implantation area of the prosthesis. This control rod 24 may likewise comprise, at its interior, a metal axial bore 52 which stiffens it slightly and is in the shape of an extended hollow tube delimiting the passage 50 in the interior.

With respect to FIGS. 1 to 7, there will now be described the application of the device for an implantation of the filter 1, by the femoral route, into the inferior vena cava 2, slightly below the kidneys, the patient being at least locally anaethetised.

Firstly, the operating surgeon may either commence by providing a percutaneous access route to the left internal femoral artery 4 in the thigh, or by "stripping" this vein.

He then introduces the guide thread 10 into the vein 4, until it reaches the inferior vena cava 2, a little beyond the implantation area The operating surgeon then enlarges, By a small incision, the entry orifice 7 of the wire 10 and then he fits, on the proximal end this thread which projects from the femoral vein, the assembly consisting of the guide 20 introduced into the sheath 8 (the length $L_g$ of which is then of course at least equal to the distance between the "puncture" area 7 or the area of insertion of the device into the body, and the area 6).

It is then necessary to lower this assembly along the thread 10, until the radio-opaque marker 34 of the guide reaches the area 6; after which the thread 10 and the guide 20 may be withdrawn, the sheath thus being in position.

After having secured the syringe body 42 containing the radially restricted filter 1 onto the connecting piece 38, the operating surgeon may then slide the filter (still in its retracted state) by means of the control rod or pusher 24, in the direction of the distal end 82 of the sheath, in order to expel it in the area 6 of the vein.

In the case of a procedure of this type, an "asymmetrical" opening of the filter, in which some of the fingers become anchored more rapidly than others, has occurred in certain cases, There may result in an oblique and relatively incorrect position of the filter in which the appendages 14a, 14b, and 14c, which are the closest to the wall during the ejection, appear relatively grouped together in relation to three other appendages 14d, 14e, 14f (see FIG. 1).

Being of the opinion that the incorrect opening of the filter may be due to a problem of positioning the sheath, the inventors have concentrated on modifying this positioning. They have thus established that, in certain cases and as may be seen in FIG. 7, the sheath, in position in the body, naturally presses itself, at least towards its distal end 82, against the wall 21 of the vena cava, with its axis 81 offset in relation to the axis 22 of the vein.

To remove this disadvantage and permit a correct implantation of the filter in the vein, the invention proposes a new device comprising centering means 54. These means, which are provided here in order to be located in the interior of the sheath over at least a part of its length, will act on the profile of the axial line of this sheath by forcing its distal end 82 to direct itself towards the axis of the vein, when the sheath is disposed therein. Advantageously, these means, which are supple or deformable, are mounted in a sliding manner in the interior of the sheath and optionally in the control rod if this latter is hollow, to thus exert a force on the sheath which force tends to modify the direction of its end 82. As shown in FIG. 8, these means also permit, as a function of their axial and angular position inside the sheath, the curvature of this latter to be varied along the axial line 81 thereof.

Referring now to FIG. 9, these centering means may consist of a cable 54 which is flexible and resiliently deformable, preferably naturally having a rigidity greater than or equal to that of the sheath and/or the stem 24. Advantageously, this centering cable may be a single metal thread, for example of stainless steel or of "PHYNOX" (Trade Mark).

The cable may be subjected to conventional treatment, in such a manner as to ensure that it has a naturally curved shape, a priori different from that of the sheath (normally already in position in the vessel) and in any case such that the cable may only be displaced in the narrow axial passage inside this sheath in a restricted state, imposing a reaction as regards the profile of its axial line (by means of the hollow rod 24 when the cable is introduced therein).

The cable may furthermore comprise, at its distal end 58, a rounded end 68, and be terminated, at its proximal end 62, by a widened handle 66, for holding the cable in the hand, thus preventing it penetrating into the sheath or the rod beyond the desired distance.

The length $L_c$ of the cable along its axis 56 is, a priori, less than or equal to that of the rod 24 and less than that of the sheath, since it is preferable that the cable does not project beyond its distal end 82.

Still with reference to the illustration in FIG. 9, the centering cable 54 which is here shown in its natural, non-restricted state, has, from its proximal end 62, a part which is substantially rectilinear and which is followed, towards the end 58 and along the length, end part 60 which is curved in a regular manner (and has substantially constant radius of curvature R). The length $l_c$ of which is preferably between one quarter and two thirds of the total length $L_c$. The same as R, is in this case, sufficiently large in relation to $L_c$ for the cable, when it is inserted into the sheath, to act in an appropriate manner on the axial profile.

The cable 54, which is resiliently deformable along the axial line 56, advantageously has a flexibility which is substantially constant and a construction which is the same over the entire length thereof $L_c$. Preferably it is advisable to use a cable which can be inserted, not only into the sheath but also into the control stem which is then provided with its interior passage 50. In this case, care is taken to use cable with an exterior diameter which is slightly less than the interior diameter of the pusher 24 so the cable can only slide therein tightly and under restraint.

Referring now to FIGS. 10 and 11, there will be described a possible use of a cable 54 of this type.

when the sheath 8 has been placed in position, as described above, the rod 24 pushes the filter 1 in the interior of the sheath in the direction of the end 82 thereof, but it stops in the vicinity of this end and without exiting from the sheath.

The subsequent operation consists in introducing the cable 54, via the hollow connection piece 46, into the passage 50 of the rod, up to an interior area 70 of the sheath which is located just before its distal end part 82a then supporting the filter, slightly upstream of the area of implantation 6 and substantially at the location of the second turn 72 which this sheath makes, and in the vicinity of or lust after the connection of the two iliac veins 5a and 5b (FIG. 8). It is furthermore substantially from this area 70 that the device is pressed against the wall of the vessel, before the introduction of the cable 54. Thus, by making the insertion of the cable in the area 70 deeper or more shallow, i.e. by a movement in translation of this cable in the passage 50, it will be possible to act on the axial orientation of the end 82. This end is free as regards movement, of the sheath by directing it towards the axis 22, at a distance, from the area 70 (the effect produced taking into account in particular the reaction of the sheath and the wall of the vessels against which the sheath is supported, at least locally).

The operating surgeon can check all the operations perfectly using known methods such as radiography.

When the operating surgeon judges that the distal end of the sheath is positioned correctly in the vein, he then blocks the movement of the cable in relation to the rod (and to the sheath). He may then expel the filter by acting only on the sheath by pulling slightly backwards, drawing it towards him. The ejection direction of the filter being substantially in the extension, or at a very close angle thereto, of the axis o the vessel during its opening, the filter must thus position itself correctly, as is shown in FIG. 11, with its axis 18 substantially merged with that of the vein.

It only remains to withdraw the assembly consisting of the sheath, the rod and the cable and to close, in the conventional manner, the incision that has been made.

By way of example, it should be noted that the sheath 8 may have a length of the order of 60 to 70 cm, the guide thread, the mandril and the control rod preferably being slightly longer. The centering cable may, in itself, have a length $L_c$ of between approximately 70 and 90 cm, with a diameter of the order of 1 mm, a radius of curvature R of approximately 20 to 60 mm and a curved end part 60 defining an angle of between approximately 90° and 180°. The exterior diameter of the sheath on the one hand, and of the mandril and the control stem on the other hand, may, respectively, be of the order of 4 mm and 3 mm, the diameter of the guide thread being of the order of 0.5 to 1 mm.

The invention, of course, is not limited to the embodiment described here.

For example, it may be envisaged that the centering means consist of a cable, designated in FIGS. 12 and 13, which may be produced of materials with a shape memory, such as thermal shape memory alloys which undergo a transition between an austenitic state and martensitic state at certain temperatures. When the alloys are deformed, ie. when they are in their martensitic starer they retain this deformation for as long as they remain in this state; they return to their first shape when they are heated to a transition temperature which is sufficient for them to return to an austenitic state. The temperatures at which these changes of state are produced depend in particular on the nature of the alloy. For example, in the case of alloys based on titanium and nickel, such as "Nitinol" (registered trade mark, alloy based on approximately 50% titanium and 50% nickel), the transition temperature is close to that of the human body (usually from approximately 36° C. to 38° C.), and thus the cable 54' has a different flexibility depending on whether it is disposed for a given time in the interior of the body of the patient or outside it.

The cable 54' may be treated, in a manner known per se, to be supple and deformable, as is shown in FIG. 12, at a temperature which is close to the ambient temperature (in the vicinity of 25° C.). It tends adopt naturally, when once it is in position in the duct, via the sheath, and heated to a temperature close to that of the body of the patient, while preserving a certain elasticity, a curved form defined during the preliminary treatment, such as is shown in FIG. 13. A cable of this type can easily be introduced into the sheath until it is close to the area 70 thereof, upstream of the end distal part 82a thereof, since it adapts perfectly to the trajectory followed by the sheath. Once introduced, it reheats progressively on contact with the sheath, (and with the hollow rod) which is (are) kept at temperature by the blood of the patient, which initiates a change in its shape: the cable returns to the curvature defined during its treatment which thus allows the operating surgeon to direct, from a distance, the distal end of the sheath towards the axis of the duct to "release" a filter of this type in a substantially central position.

According to a further embodiment of the invention, the cable 54 having a naturally curved shape, may be produced from a material with a shape memory; this material having very high properties of elasticity optionally associated with properties of shape memory. The above-mentioned alloys of the "Nitinol" type also have, in their resilient phase (austenitic structure) a resilient draw out rate of between approximately 5 and 10%, and preferably 6 and 8%, this rate corresponding to the formula $(d_{max}-d) \times 100/d$, d being the nominal length, without axial tension of a sample produced from a shape memory alloy, $d_{max}$ being the maximum length of this same sample under axial constraint up to the limit of the area of elasticity, the result being expressed in percent (%).

According to a further embodiment, the sheath 8 may comprise a supple tube of which at least one tubular part, located in the distal area of the sheath, is provided from a shape memory material, this part constituting said centering means of the device.
Thus, during the introduction of the sheath into the body of the patient, the part produced from a shape memory material is progressively warmed by the blood of the patient until the transition temperature of this material, this part then tending to assume a curved shape (defined during a preliminary treatment which is known per se) permitting at least the distal end of the sheath to be drawn away from the wall of the vessel while being directed towards the axis of the duct. The position of this end may subsequently be corrected, if necessary, for example, by means of a control rod introduced into the sheath or a metal cable.

Furthermore, it may also be envisaged that a device for implanting filters, called Mobin-Uddin, which may be positioned by the known seldinger method (cf. for example U.S. Pat. No. 4,727,873) be used. A device of this type comprises a sheath, designated 8' in FIG. 14, which comprises a principal tubular part 8a extending along the axis 81' from the proximal end 83' of the sheath and being extended by a tubular end part 8b'. For example, the principle part, the exterior and interior diameters of which are, respectively, less than those of the part 8b', may be produced from a flexible material such as a biocompatible plastics material, the end part being rigid and metallic (for example of stainless steel). This part 8b', which is shorter than the part 8a', has a length which is adopted to completely accommodate the filter in a retracted state, this filter being positioned in this part 8b' at the vicinity of the distal end 82', prior to the introduction of the sheath into the body of the patient. As regards the control stem 24' of the device, which is filter at least in part, it is extended at its distal end 24b' by a hollow widened part 25', the diameter of which is greater than that of the rod and of course slightly less than the interior diameter of the end part of the sheath, forming a support surface or piston which is relatively strong to expel the filter to the outside of the sheath more easily. The sheath, in which the rod is disposed and which contains the filter, introduced into the body of the patient up to an area at which the filter is implanted in a manner known per se.

It should be noted that, in the case of temporary filters without means of anchoring in the wall, the device according to the invention may be used both to implant and/or to remove the filter.

We claim:

1. A device kit for implanting a medical assembly in a duct of a human or animal body, said duct having an axis, said device comprising:

a tubular implantation sheath adapted for containing said assembly to be implanted, said sheath having a length along an axial line, a distal end, an internal diameter, and being flexible at least over a part of its length;

a hollow tube for controlling movement of the assembly in said sheath, said tube being at least partly flexible, and having external and internal diameters, the external diameter of the tube being less than the internal diameter of said sheath, for being slidingly inserted therein; and a resiliently deformable centering cable having
   (a) a naturally curved axial line:
   (b) a length along the axial line, said length being less than that of the sheath; and
   (c) an external diameter which is slightly less than said internal diameter of said hollow tube;

so that the cable is adapted to be inserted axially in the hollow tube in a constrained state, and to slide coaxially therein for exerting, through said hollow tube and because of its natural curved line, an internal force on the flexible part of the sheath, tending, by reaction and as a function of the insertion of said cable and said tube in the sheath, to act on the profile of the axial line of said sheath and vary the direction of its distal end.

2. The device according to claim 1, wherein the cable is made of a thermal shape memory material.

3. The device according to claim 1, wherein the cable is made of an alloy comprising approximately 50% titanium and 50% nickel.

4. The device according to claim 1, in which the axial resilient extension ratio of the cable is between approximately 5% and 10%.

5. The device according to claim 1, wherein said sheath is flexible along its length, and free of any rigid distal end part.

6. The device according to claim 1, in which the cable is disposed exclusively in said flexible part of said sheath.

7. The device according to claim 1, in which the centering cable comprises a first proximal part which is substantially rectilinear and a second distal part which is curved and disposed proximate the distal end of the sheath.

8. A device for implanting a medical assembly in a duct of a human or animal body, said duct having an axis, the device comprising:

a tubular implantation sheath containing said assembly to be implanted, the sheath having a length along an axial line, a proximal end and a distal end, and being flexible at least over a part of its length;

a hollow tube for controlling movement of the assembly in the sheath, said tube being at least partly flexible, and being slidably inserted in the sheath, through the proximal end thereof, to slide coaxially therein with a slight radial play;

a resiliently deformable centering cable having a naturally curved axial line, said cable being slidably inserted in the hollow tube, to slide coaxially therein with a slight radial play for exerting, through the hollow tube and because of the natural curved line of the cable, an internal force on the flexible part of the sheath, so as to act, as a function of the insertion of the cable in the hollow tube and of the hollow tube in the sheath, on the profile of the axial line of the sheath and vary the direction of the distal end thereof; and means for preventing the cable from extending beyond the distal end of the sheath.

* * * * *

UNITED STATES PATENT AND TRADEMARK OFFICE
CERTIFICATE OF CORRECTION

PATENT NO. : 5,630,801
DATED : May 20, 1997
INVENTOR(S) : Maurice Roussigne et al.

It is certified that error appears in the above-indentified patent and that said Letters Patent is hereby corrected as shown below:

At col. 6, line 15, before "end part", insert --by an--.

Signed and Sealed this

Twenty-sixth Day of August, 1997

Attest:

BRUCE LEHMAN

Attesting Officer

Commissioner of Patents and Trademarks